United States Patent [19]

Imran et al.

[11] 4,393,877

[45] Jul. 19, 1983

[54] HEART RATE DETECTOR

[75] Inventors: Mir Imran, Pittsburgh; Steve Kolenik, Leechburg, both of Pa.

[73] Assignee: Mieczyslaw Mirowski, Owings Mills, Md.

[21] Appl. No.: 263,910

[22] Filed: May 15, 1981

[51] Int. Cl.³ ............................................. A61B 5/04
[52] U.S. Cl. ................................ 128/705; 128/419 D
[58] Field of Search ........ 128/419 P, 419 PG, 419 D, 128/700, 702, 704, 705, 706, 670, 708

[56] References Cited

U.S. PATENT DOCUMENTS

| | | | |
|---|---|---|---|
| Re. 27,652 | 5/1973 | Mirowski et al. | 128/419 D |
| Re. 27,757 | 9/1973 | Mirowski et al. | 128/419 D |
| Re. 30,372 | 8/1980 | Mirowski et al. | 128/419 D |
| 3,577,983 | 5/1971 | Baessler | 128/704 |
| 3,590,811 | 7/1971 | Harris | 128/708 |
| 3,608,545 | 9/1971 | Novack et al. | 128/705 |
| 3,823,708 | 7/1974 | Lawhorn | 128/705 |
| 3,857,398 | 12/1974 | Rubin | 128/419 D |
| 4,184,493 | 1/1980 | Langer et al. | 128/419 D |
| 4,202,340 | 5/1980 | Langer et al. | 128/419 D |
| 4,291,699 | 9/1981 | Geddes et al. | 128/419 D |

OTHER PUBLICATIONS

Ottonello, "A Device for Probability Density Function Measurements", *J. of Physics E,* vol. 7, #11, pp. 878–879, Nov. 1974.
Mims, *Engineers Notebook: A Handbook of Integrated Circuit Applications,* ©1979, Radio Shack, a Div. of Tandy Corp., pp. 64, 66, 68.
Senczuk, "Description of a 15 Channel Analog Selector", IEEE Trans. Biomed. Eng., vol. BME 24, #2, Mar. 1977.

*Primary Examiner*—William E. Kamm
*Assistant Examiner*—Mitchell J. Shein
*Attorney, Agent, or Firm*—Fleit, Jacobson & Cohn

[57] ABSTRACT

A heart rate detector apparatus, particularly for use in an implantable defibrillator, is disclosed. The heart rate detector apparatus includes two distinct detector circuits each responsive to ECG waveforms of different characteristics. One of the detector circuits is responsive to ECG waves having slew rates above a predetermined threshold. The other detector circuit is responsive to ECG waves having lower slew rates, such as ECG waves of more sinusoidal shape. A coupling circuit automatically couples one of the two detector circuits to an output circuit, such as a heart rate comparator. In a specific embodiment, the heart rate comparator determines the heart rate, compares the heart rate with a predetermined rate, and, if the heart rate exceeds the predetermined rate for a predetermined time period, provides an output signal. The output signal may be used to enable a defibrillating circuit to deliver a defibrillating shock to the patient.

37 Claims, 2 Drawing Figures

HEART RATE DETECTOR

BACKGROUND OF THE INVENTION

1. Field of the Invention

The present invention relates to a heart rate detector system, and more particularly, to an improved heart rate detector capable of use with an implantable defibrillator for defibrillating the heart of a patient when the patient experiences a life-threatening arrhythmia.

2. Description of the Prior Art

In recent years, substantial progress has been made in the development of defibrillation techniques for providing an effective medical response to various heart disorders or arrhythmias. Earlier efforts resulted in the development of an electronic standby defibrillator which, in response to detection of abnormal cardiac rhythm, discharged sufficient energy, via electrodes connected to the heart, to depolarize the heart and restore it to normal cardiac rhythm. Examples of such electronic standby defibrillators are disclosed in commonly assigned U.S. Pat. Nos. 3,614,954 (subsequently, Re. 27,652) and 3,614,955 (subsequently, Re. 27,757).

Past efforts in the field have also resulted in the development of implantable electrodes for use in accomplishing ventricular defibrillation (as well as other remedial techniques). In accordance with such techniques, as disclosed (for example) in U.S. Pat. No. 4,030,509 of Heilman et al., an apex electrode is applied to the external intrapericardial or extrapericardial surface of the heart, and acts against a base electrode which can be either similarly conformal or in the form of an intravascular catheter. Such electrode arrangements of the prior art, as disclosed in the aforementioned patent of Heilman et al., can employ independent pacing tips associated with either a base electrode or an apex electrode, or both.

Recent efforts also have resulted in the development of techniques for monitoring heart activity (for the purpose of determining when defibrillation or cardioversion is necessary), which techniques employ a probability density function for determining when ventricular fibrillation is present. Such a technique, employing the probability density function, is disclosed in U.S. Pat. Nos. 4,184,493 and 4,202,340, both of Langer et al.

In accordance with this latter technique of the prior art, when the probability density function is satisfied, fibrillation of the heart is indicated. However, recent experience has shown that, with certain unusual ECG patterns, the prior art probability density function detector, if not optimally adjusted, can be "triggered" not only by actual ventricular fibrillation, but also by some forms of high rate ventricular tachycardia, and low rate ventricular tachycardia as well, particularly in the presence of ventricular conduction abnormalities. The possibility of such triggering in the presence of some high rate tachycardia is acceptable because high rate tachycardia often can be fatal if present at such a rate that sufficient blood pumping no longer is accomplished. However, triggering in the presence of non-life threatening, low rate tachycardia could be considered a problem. Therefore, it has been determined that there is a need for a system and method for distinguishing between ventricular fibrillation and high rate tachycardia, on the one hand, and low rate tachycardia, on the other hand.

One response to the need discussed above is described in commonly assigned co-pending patent application Ser. No. 175,670 filed on Aug. 5, 1980, entitled "Arrhythmia Detection System And Method" (Langer et al.). There, a probability density function circuit, responsive to differentiated ECG signals from the heart electrodes, is used in conjunction with a heart rate circuit whereby the probability density function (PDF) circuit activates a defibrillator pulse generator only when the PDF circuit is enabled by the heart rate circuit. Such enabling occurs when the heart rate exceeds a predetermined value reflecting what is considered to be a dangerous high rate tachycardia.

The success of the latter system depends, in large part, on the reliability and accuracy of the heart rate detector circuit. Heart rate detectors, per se, are known in the art. Such heart rate detectors are typically designed to be responsive to incoming ECG waveforms of a predetermined type. For example, it is known to detect a heart rate by the use of a zero-crossing detector. In such detectors, the zero-crossing points of the ECG waveform reflect a periodic event in the cardiac cycle. When, however, the ECG waveform is characterized by rather steep slopes, for example when the rate of change of the R-wave voltage is steep, or spiky, then the use of such a system to detect the zero-crossings loses accuracy. The steep slope R-wave complex, with its accompanying Q and S segments, results in multiple counts per cardiac cycle, giving an artificially high rate reading, which could, in certain cases, be significant.

It is also known in the art to provide a heart rate detector responsive to those ECG signals having steep or "spiky" slopes. Some such detectors respond to the ECG signal and provide an output responsive to such steep slope signals. Such output may be provided by a slew rate detector which compares the slope, or slew rate, with a slew rate threshold and provides an output signal reflecting the number of high slew rate signals detected. A problem inherent in such a system is the detection of a heart rate when the ECG signal is more sinusoidal than spiky. In such cases, the slew rate, or rate of change of the ECG voltage versus time, characteristic is small. Thus, the detector may not pick up such signals, thus, resulting in detection of an inaccurate low heart rate.

In very ill patients, it is not unusual to find that the ECG waveforms change from time-to-time. The ECG could present itself as a spiky waveform for a time, and then become more sinusoidal, or vice versa. Rate detectors, of the types described above, would not be versatile enough to effectively respond to both types of ECG waveforms.

It is thus seen that the prior art heart rate detectors fail to provide the required flexibility in monitoring ECG signals characterized by both spiky ECG waveforms and the more sinusoidal ECG waveforms. Prior art detectors can be designed to work very efficiently with one or the other of such waveforms, but not both. Therefore, it has been determined that a need exists to provide a flexible, accurate and reliable heart beat rate detector that is operable over a broad range of detected ECG waveforms.

SUMMARY OF THE INVENTION

According to the present invention, there is provided a heart rate detector system that results in a highly accurate measurement of the heart rate for a variety of monitored ECG signal shapes. Such heart rate detector has particular utility in an automatic implantable defibrillator system wherein the heart rate detector is used in conjunction with a probability density function circuit, such combination as described in the co-pending Langer et al. patent application. However, it should be noted that the heart rate detector of the present invention also has significant utility in a heart pacing system or in any other environment where the heart rate is required to be reliably, efficiently and accurately measured.

The heart rate detector of the present invention is responsive to an incoming ECG signal having a series of wave packets, each wave packet including P, Q, R, S and T waves, as is well-defined in the art. The heart rate detector includes two mutually exclusive detection circuits that are responsive to incoming ECG waves having different characteristics. These detection circuits are coupled with an output circuit. Depending upon the incoming ECG wave characteristic, the coupling circuit automatically and selectively couples one of the two detection circuits with the output circuit to provide an accurate count of the heart rate.

In particular, the two mutually exclusive detection circuits of the present invention include a high slew rate detector, and an amplitude threshold detector. When the incoming ECG wave is characterized by spiky waves having a high slew rate, the high slew rate detector is coupled with the output circuit. When the incoming ECG wave is characterized by lower slope, or more sinusoidal, ECG signals, then the threshold amplitude detector is coupled with the output circuit.

More particularly, when the incoming ECG waves have a slew rate above a predetermined level, and such "high" slew rate signals occur at a predetermined frequency over a predetermined time, in a manner as will be described herein, then the slew rate detector circuit provides an accurate determination of the heart rate. If, however, the incoming ECG waves have a slew rate below the predetermined level, and such "low" slew rate signals occur at a predetermined rate, then the amplitude threshold detector circuit provides an accurate determination of the heart rate.

The preferred embodiment of the present invention provides an input for receiving an ECG signal. A slew rate detector circuit is coupled with the input for detecting an ECG wave shape having a slew rate above a predetermined threshold and providing an output signal for each detected wave shape. Also coupled with the input is an amplitude threshold detector circuit that detects an ECG wave shape having a predetermined amplitude and provides an output signal for each detected wave shape. An output circuit is provided to receive the two detector output signals. A coupling circuit selectively couples only one or the other of the detector circuits with the output circuit. The high slew rate detector circuit is coupled with the output circuit when a predetermined number of high slew rate signals from the slew rate detector occur at a substantially constant frequency over a first predetermined time period. When such conditions occur, the high slew rate detector remains coupled with the output circuit for as long as high slew rate signals occur within at least a second predetermined time period. At all other times, the output circuit is coupled with the amplitude threshold detector.

It is an object of the present invention to provide a heart rate detector system, more particularly, a heart rate detector system that is accurate, reliable and flexible over a broad range of detected ECG waveforms.

It is a further object of the present invention to provide a heart rate detector system that is implantable in the body for use in conjunction with an implanted electronic device such as a defibrillator or a pacer.

It is a further object of the present invention to provide a heart rate detector that is particularly suitable for use with an implantable defibrillator circuit employing a probability density function circuit whereby the probability density function circuit is enabled by the heart rate detector to ensure that a defibrillating shock occurs only during fibrillation or high rate ventricular tachycardia.

In particular, it is an object of the present invention to provide a heart rate detector that is responsive to spiky, high slew rate ECG signals, as well as the more sinusoidal ECG signals, and to provide a means for determining the heart rate reliably, accurately, and independently of which type of ECG waveform is presented.

It is an additional object of the present invention to provide a heart rate detector circuit including a high slew rate detector and an amplitude threshold detector and means for selectively and automatically switching between the two detector circuits depending upon the ECG input characteristic.

It is an additional object of the present invention to provide a heart rate detector circuit including an output circuit that provides a readout of instantaneous heart rate, and further provides a comparison between instantaneous heart rate and a predetermined, or preprogrammed, heart rate.

These and other objects of the invention will be more clearly understood by reference to the following description, the appended claims, and the accompanying drawings.

DETAILED DESCRIPTION

Figure 1:
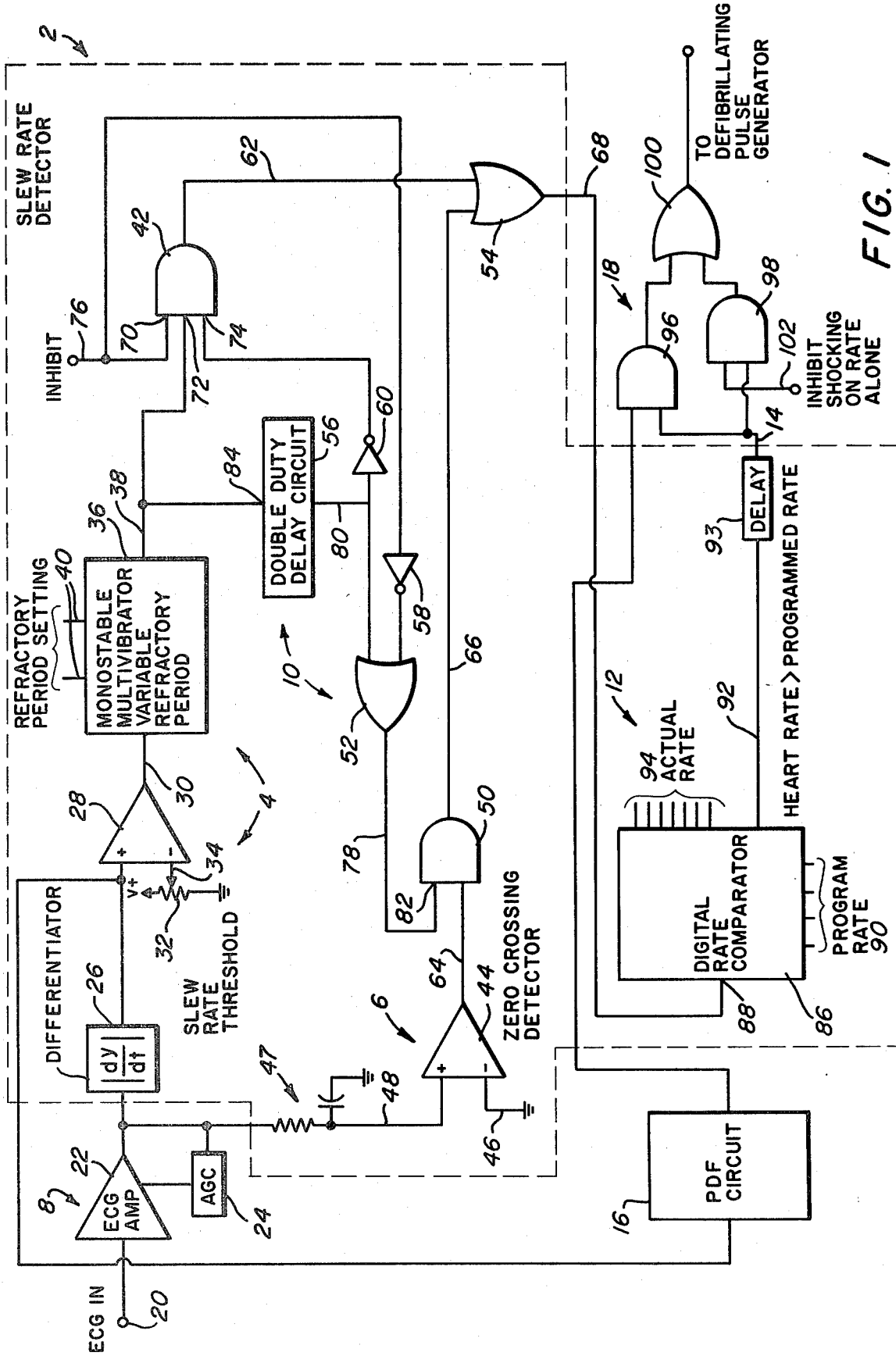
FIG. 1 is a block diagram of the heart rate detector of the present invention in a defibrillator circuit.

The heart rate detector 2 of the present invention responds to amplified, incoming ECG waveforms and includes a slew rate detector 4 and an amplitude threshold detector 6, each coupled with an input circuit 8 that provides the amplified ECG waveforms. One or the other of these detectors 4 and 6 is coupled, via a coupling circuit 10, with a digital rate comparator output circuit 12 depending on the characteristics of the ECG waveforms. The comparator output circuit 12 processes the aggregate signals received from the slew rate detector 4 and amplitude threshold detector 6 (the total signals reflecting the number of heart beats), and provides a detector output signal (on line 14) when the heart rate exceeds a predetermined, or preprogrammed, rate over a predetermined period of time.

The heart rate detector 2 may have utility in a broad range of applications, such as implantable defibrillators or pacers, or external monitoring equipment. A heart rate detector in a defibrillator circuit is shown. In particular, a probability density function circuit 16 is provided having its input responsive to an amplified and differentiated ECG signal. Logic circuitry 18 interconnects the PDF circuit output with the heart rate detector output such that the PDF circuit 16 is coupled with the defibrillating pulse generator (not shown) only upon occurrence of a detector output signal, which reflects high rate tachycardia. Details of the circuitry will now be described.

ECG input terminal 20 is coupled to suitable heart electrodes (not shown), via an interface (not shown), to receive an ECG input signal. The heart electrodes may include a superior vena cava (or base) electrode and an apical cup (or patch) electrode in association with a patient's heart. Such electrodes are schematically shown in the co-pending Langer et al. patent application, incorporated by reference herein.

The incoming ECG signal includes a series of wave packets reflecting heart beats, each wave packet including P, Q, R, S and T waves as is understood in the art. Each wave packet defines a cardiac cycle, as the term is used herein.

The input terminal 20 is connected with a conventional ECG amplifier 22 having an automatic gain control (AGC) circuit 24. In this manner, input signals of different amplitudes can be handled by the overall circuit, as is well known in the art.

Connected to the ECG amplifier 22 are the two detector circuits 4 and 6 of the present invention. The slew rate detector 4 includes a differentiator and absolute value circuit 26 which takes the absolute value of the first derivative of the incoming amplified ECG signal. This absolute value of the first derivative is defined as the slew rate, which is the instantaneous rate of voltage change per unit of time. In the context of the present invention, the slew rate can be suitably measured in terms of microvolts per millisecond. The differentiator and absolute value circuit 26 is conventional and known to those of ordinary skill in the art.

The slew rate value from the differentiator 26 is provided as an input to a conventional threshold comparator 28. The slew rate is compared with a predetermined slew rate threshold value. When the slew rate exceeds the slew rate threshold, a slew rate output signal is provided on the comparator output line 30. The slew rate threshold is predetermined before the unit is implanted and is set by adjusting the variable resistor 32 connected to the negative input terminal 34 of the comparator 28. (It is envisaged that slew rate also can be set, or programmed, from outside the body by telemetry or other appropriate techniques.) The slew rate threshold may be set depending upon the ECG characteristics of the particular patient, but typically should be set so as to provide a slew rate output signal only for relatively high slew rates, i.e., slew rates resulting from ECG signals of relatively spiky, or high slope, angles.

The slew rate output signals are provided over line 30 to the input of a monostable (one-shot) multivibrator 36 having a variable refractory period. The monostable multivibrator 36 provides a uniform output pulse on line 38, as is well known in the art. This output pulse is defined herein as the wave detector, or slew rate detector, output signal, or pulse.

It is desirable, for proper operation of the system, that only one wave detector output signal be provided in a single cardiac cycle in order that the wave detector output signal properly represents the number of heart beats. As stated above, each cardiac cycle includes a wave packet of P, Q, R, S and T waves. Generally, only the R wave slew rate will be sufficiently high to provide a slew rate output signal from the comparator 28 to the monostable multivibrator 36. However, for certain patients, one of the other waveforms within the wave packet, particularly the P or T waves, might also have a high slew rate such that the slew rate threshold value set by the variable resistor 32 is exceeded. Thus, more than one slew rate output signal per cardiac cycle may be provided as the input to the monostable multivibrator, which, in turn, would result in multiple wave detector output signals on line 38 for only a single heart beat.

In order to avoid the potential problem set forth above, the refractory period of the monostable multivibrator 36 is adjusted, via input terminals 40, so that when a slew rate output signal from comparator 28 triggers the monostable multivibrator 36, subsequent slew rate output signals occurring within a predetermined refractory time period do not further trigger the multivibrator. The refractory period is set so that only one slew rate output signal within a wave packet, or cardiac cycle, will trigger the multivibrator 36. Once triggered, the multivibrator trigger point is inhibited for a certain refractory period, typically, between 100 and 200 milliseconds. This rate can be set depending upon the patient's normal heart rate. If the patient has a relatively low heart rate, then the refractory period should be set higher than would be the case for a patient with a high heart rate. Similarly, if the patient has a high heart rate, then the refractory period is set lower, to ensure that each slew rate output signal from the slew rate threshold comparator 28 is counted.

Generally, the refractory period is preset for a particular patient prior to implantation. However, an automatic variable refractory period adjustment mechanism may be provided, and implanted, to vary the refractory period depending upon heart rate changes.

The monostable multivibrator 36 of the present invention is a conventional circuit and its design is known to one of ordinary skill in the art. The multivibrator 36 provides a uniform pulse output on line 38 (the wave detector output signal or pulse). The width of the output pulse should not be so wide that the monostable multivibrator 36 does not reset in time to receive subsequent slew rate output signals from the comparator 28 indicative of subsequent heart beats. Similarly, the pulse width should not be so narrow that the multivibrator is retriggered upon receipt of a subsequent slew rate output signal within the same wave packet.

The wave detector output signal from the monostable multivibrator 36 is provided on the output line 38 of the monostable multivibrator, which line 38 is coupled with an AND gate 42 of the coupling circuit 10, to be described further below.

The second detector circuit of the present invention is the amplitude threshold detector 6. This threshold detector 6 includes a conventional high gain amplifier 44 having one input 46 grounded and the other input 48 connected with the ECG amplifier via a low-pass filter 47. The low-pass filter 47 filters out ECG waveforms having "spiky" characteristics and passes only the more sinusoidal ECG waveforms. The amplifier 44 responds to amplified ECG signals having an R-wave greater than a predetermined value. When the amplified ECG signal exceeds the threshold, which is arbitrarily chosen as ground, then the amplifier 44 provides a zero-crossing output signal which is coupled to AND gate 50 of the coupling circuit 10. The threshold detector 6, having the negative input of the amplifier 44 grounded, thus operates as a zero-crossing detector.

The coupling circuit 10 will now be described. Coupling circuit 10 is defined herein as the logic circuit comprised of AND gates 42 and 50, OR gates 52 and 54, double-duty delay circuit 56, and inverters 58 and 60. These circuit elements are interconnected in such a manner that the outputs of the slew rate detector circuit 4 and amplitude threshold, or zero-crossing, detector 6 are coupled with the digital rate comparator output circuit 12. AND gate 42 receives the wave detector output signal over line 38. The AND gate 42 output line 62 is connected to the input of OR gate 54. Similarly, the amplitude threshold, or zero-crossing, detector 6 output is connected, via line 64, to the input of AND gate 50. The AND gate 50 output line 66 is coupled to the OR gate 54. As will be described hereinbelow, only one of AND gates 42 and 50 is enabled at the same time and thus the OR gate 54 receives either the zero-crossing output signals (over line 66) or wave detector output signals (over line 62) depending upon which of AND gates 42 and 50 is enabled. The OR gate 54 output is provided, over line 68, to the digital rate comparator output circuit 12. The signals from the output of OR gate 54 reflect the number of heart beats detected.

AND gate 42 has three inputs 70, 72, 74. One of the inputs 72 is connected to the output line 38 from the monostable multivibrator 36 and receives the wave, or slew rate, detector output signals. Input 70 of the AND gate 42 is connected to a slew rate detector inhibit line 76. If, under certain circumstances, it is desired to monitor ECG signals solely using the zero-crossing detector 6, a zero input over line 76 to the AND gate 42 may be provided which will disenable the AND gate 42. Such inhibition of the slew rate detector may be justified depending upon the ECG waveforms of a particular patient. If the slew rate detector circuit 4 is to be maintained in the system, then the input terminal 70 of the AND gate 42 is at a high or "1" state. The third input terminal 74 of the AND gate 42 is coupled with a double-duty delay circuit 56 via an invertor 60.

The double-duty delay circuit 56 is designed such that its output 80 is normally at high, or "1," state. The "1" state is inverted by inverter 60 so that the AND gate terminal 74 has a low, or "zero" state, and AND gate 42 is disabled. The output of the delay circuit 56 is also coupled to an OR gate 52 which has an output line 78 coupled with AND gate 50. When the double-duty delay output 80 is in a high, or "1," state, the "1" signal is transferred through the OR gate 52 over line 78 to the input terminal 82 of the AND gate 50, thus enabling the AND gate 50 to pass zero-crossing output signals from the zero-crossing detector 6 to the OR gate 54 and, in turn, to the digital rate comparator 12. On the other hand, when the double-duty delay circuit output 80 is low, or in a "0" state, the third terminal 74 of the AND gate 42 is enabled, and the terminal 82 of the AND gate 50 is disenabled. Wave, or slew rate, detector output signals from the monostable multivibrator 36 are thus coupled through AND gate 42 to OR gate 54 and, in turn, to the digital rate comparator output circuit 12. It is thus seen that the double-duty delay circuit 56 alternately enables one of the AND gates 42 and 50 so that either the zero-crossing detector 6 or the slew rate detector 4 is coupled to the digital rate comparator output circuit 12.

Figure 2:
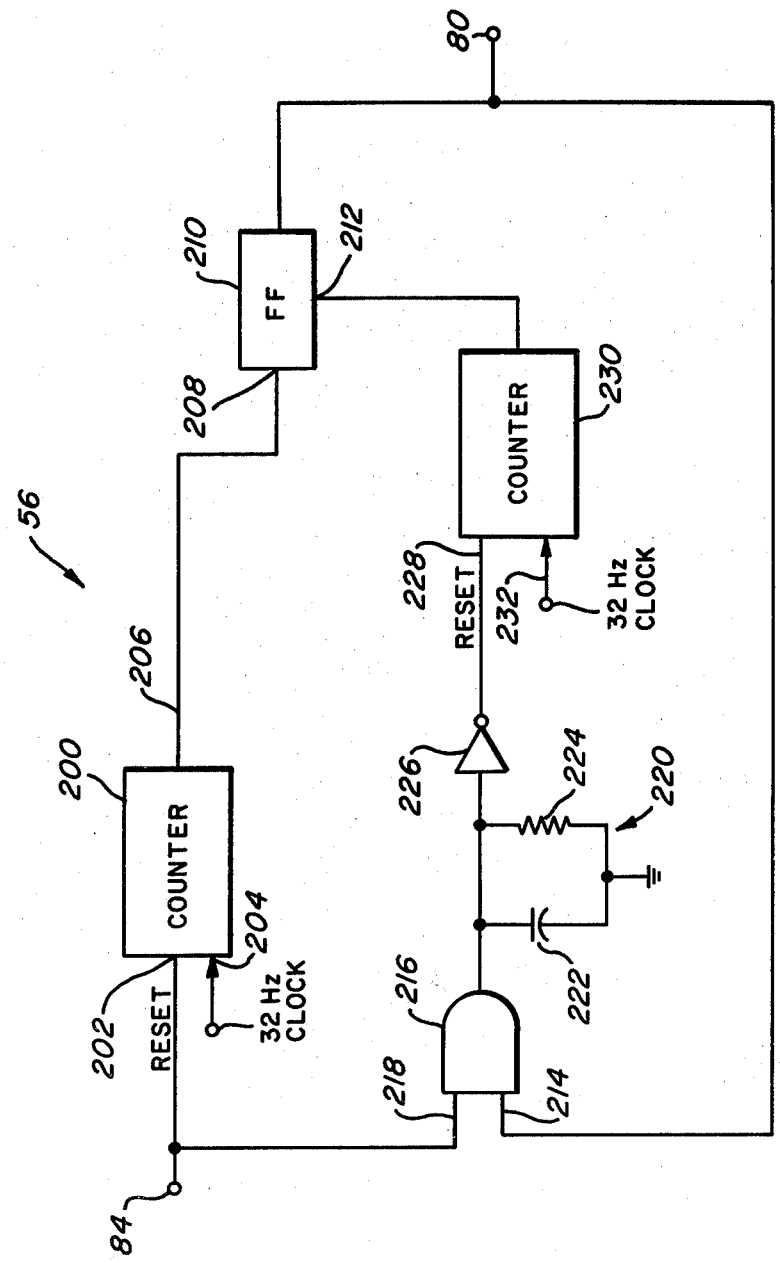
FIG. 2 is a block diagram of the double-duty delay circuit shown in FIG. 1.

The double-duty delay circuit 56 is shown in detail in FIG. 2. The circuit includes an input 84 which is coupled with the output line 38 of the monostable multivibrator 36 and thus receives wave detector output pulses from the wave, or slew rate, detector circuit 4. These wave detector output pulses are provided to input 202 of a conventional digital counter 200. The counter 200 has a second input 204 that receives clocking pulses, such as a 32 Hz clock signal. The counter 200 counts the clocking pulses and, if a predetermined number of clocking pulses are consecutively counted, the counter 200 provides a high, or "1," signal on the counter output line 206. For example, if clocking pulses provided at input 204 are counted for a predetermined time period, e.g., 2 seconds, then the counter 200 output becomes high, or in its "1" state. However, the counter 200 is reset upon receipt of each wave detector output pulse provided to input 202. When reset, the counter output is low, or in its "0" state. It is thus seen that so long as wave detector output signals from the slew rate detector circuit 4 occur within a predetermined time period, such as 2 seconds, then the counter 200 output is "0"; if no wave detector output signal is forthcoming for such 2 second interval, then the counter 200 output is "1."

The counter output line 206 is connected to input 208 of a conventional set-reset flip-flop 210. The flip-flop 210 has a second input 212 and an output 80. The output 80 is coupled to inverter 60 and OR gate 52, as described with respect to FIG. 1.

The flip-flop 210 has the following characteristics. When a high, or "1," signal is provided at input 208, the output 80 is high, or in its "1" state. When a high, or "1," signal is provided at input 212, in a manner to be described, the output 80 is low, or in its "0" state. The flip-flop 210 is controlled, and switches state, solely by "1" signals applied to one of the inputs 208 and 212.

Output line 80 is further coupled to input 214 of AND gate 216. The other input 218 of AND gate 216 is connected to input 84 to receive pulses from the slew rate detector circuit 4. Thus, when the output 80 is in its "1" state, the AND gate 216 is enabled to pass wave detector output pulses from the slew rate detector circuit 4. These wave detector output pulses are passed by AND gate 216 to an RC circuit 220.

The RC circuit 200 includes a capacitor 222 and resistor 224 connected in parallel. The output of RC circuit 220 is connected to an inverter 226. The inverter 226 output is connected to a reset terminal 228 of a counter 230, substantially identical in operation to the previously described counter 200, and including a second input 232 coupled to a predetermined clocking source, such as a 32 Hz clocking signal.

When a wave detector output pulse from the slew rate detector circuit 4 is passed by AND gate 216 to the RC circuit 220, the capacitor 222 is immediately charged and begins a gradual exponential decay, as is well known in the art. The decay time depends on the RC characteristics. In the present case, the RC characteristics are such that upon receipt of a wave detector output pulse, the capacitor 222 is substantially immediately charged to a voltage level exceeding the threshold needed for the inverter 226 to change its state. The capacitor then gradually decays until the voltage drops below the threshold. If a second wave detector output pulse is received by the RC circuit before the voltage drops below the threshold, then the inverter 226 remains in its changed state, until the voltage drops below the threshold. It is thus seen that if a predetermined number of wave detector output pulses are received by the RC circuit 220, and if these output signals are spaced apart by a predetermined time, the threshold voltage level, at which the inverter 226 is operative, will continuously be exceeded. The RC characteristic is correlated with the predetermined time period of the counter 230, as will be described below.

Let us suppose that the output 80 in its "1" state. (As described with reference to FIG. 1, when output 80 is in its "1" state, the zero-crossing detector 6 is coupled to the digital rate comparator 12.) The AND gate 216 is thus enabled to pass any wave detector output pulses that might be received from the slew rate detector circuit 4. If no wave detector output pulses are received (evidencing that the input ECG is of the low slew rate type), no voltage is presented to the inverter 226. The input of inverter 226 is thus low (below threshold), or "0." The "0" signal is inverted to provide a "1" signal at the output of inverter 226 and hence to the reset terminal 228 of counter 230. The output of counter 230 is thus "0," which is provided at input 212 of flip-flop 210. A "0" signal at input 212 does not change the state of the flip-flop, as discussed above.

Now let us suppose that a high slew rate signal is detected by the rate detector such that a wave detector output pulse is provided by the multivibrator 36 (FIG. 1) to the input 84. This signal is passed by AND gate 216 to the RC circuit 220. (Such a signal is also provided to reset input 202 of counter 200 which, in turn, provides a "0" signal on line 206 to the flip-flop input terminal 208. However, as discussed above, a "0" signal at input 208 does not change the state of the flip-flop 210 and the output 80 will remain in its "1" state.) Capacitor 222 is immediately charged above the inverter threshold voltage level and the inverter 226 now "sees" a "1" input. The "1" input to inverter 226 is inverted to a "0" output which is provided to the reset terminal 228 of the counter 230. The counter 230 thus is enabled, and begins to count the 32 Hz signals provided at its other input 232.

Let us suppose that the wave detector output signal at terminal 84 was an anomaly, and that no subsequent output signal is provided within the time period before the capacitor 222 decays below the threshold voltage level (on the order of two seconds). That is, no subsequent pulse is provided to the RC circuit 220, via the AND gate 216, before the capacitor 222 decays to a level below the threshold level. Under such circumstance, the input voltage to the inverter 226 will fall below threshold, i.e., to a "0" state, the inverter 226 output will switch back to a "1" state, and thus will reset the counter (at terminal 228). This reset will occur before the counter 230 has counted its predetermined number of clock pulses; i.e., the reset will occur before a predetermined (2 sec.) time interval. Thus, the output of counter 230 will not have changed its state to a "1" output; rather the counter 230 remains at its "0" state and the flip-flop 210 is not reset. The flip-flop 80 remains in its "1" state.

Let us now consider the condition where a second pulse from the slew rate detector circuit 4 is received by AND gate 216 before the capacitor 222 decays below the threshold voltage level. This second pulse recharges capacitor 222 to its fully charged state, such that the capacitor maintains a voltage above the inverter threshold level for a time greater than the predetermined time interval of counter 230, thus maintaining the counter 230 in its enabled state to count a sufficient number of clock pulses such that the output of counter 230 switches to its "1" state. As will be recalled, this "1" signal from counter 230, provided at input 212 of flip-flop 210, changes the flip-flop 80 to a "0" state. The AND gate 216 is now disabled. Similarly, since the output 80 is "0," the slew rate detector circuit 4 is coupled to the digital rate comparator 12 (FIG. 1). So long as further high slew rate signals are provided at least every two seconds to terminal 84, the output 80 remains at its "0" state.

From the above description, it should be apparent that to maintain the input voltage to inverter 226 above the threshold level, and hence to maintain counter 230 in its high state (so that the zero-crossing detector 6 is uncoupled from, and the slew rate detector circuit 4 is coupled to, the digital rate comparator 12), the wave detector output pulses from the slew rate detector circuit 4 must occur above a particular rate and must also occur at substantially equal spacing. For example, let us assume that the predetermined time period of the counter 230 is two seconds, and further assume that it is desirable to "switch over" to the slew rate detector circuit 4 when two consecutive wave detector output pulses are received. Upon receipt of the first wave detector output pulse to the RC circuit 220, the capacitor charges up, substantially instantaneously, to exceed the threshold voltage of inverter 226, and then begins to decay. If the second consecutive wave detector output pulse occurs ½ second later, and no further pulse is received within the 2 second window, then the voltage to inverter 226 will fall below the threshold level before the 2 second period of counter 230 is completed. The counter 230 will be reset the "instant" the capacitor voltage falls below the threshold of inverter 226, and hence will not change from its "0" state, maintaining the output 80 in its "1" state; no "changeover" to the slew rate detector circuit 4 occurs.

Similarly, if the second wave detector output pulse occurs 1½ seconds after the first, then the voltage to the inverter 226 will have decayed below threshold before the second pulse is received. Again, even though counter 230 was enabled by the first pulse, it would be reset the "instant" the capacitor voltage fell below the threshold of inverter 226 (i.e., not continuously exceeded during the 2 second window of counter 230); thus, counter 230 will not change from its "0" state.

With reference to FIG. 1, the double-delay circuit 56 functions in the following manner. Assume, as a starting point, that the zero-crossing detector 6 is coupled to the digital rate comparator output circuit 12. The double-duty delay circuit output 80 is in its "1" state. Wave detector output signals from the slew rate detector circuit 4 are now received. The double-duty delay circuit 56, over a first predetermined time period, counts the number of wave detector output signal pulses that have a relatively constant frequency. If the number of constant frequency, i.e., substantially uniformly spaced, pulses exceeds a predetermined number within the first predetermined time period, then the double-duty delay output line 80 is shifted from a normally high to a low, or "0" state. It remains in this "0" state for at least a second predetermined time period. The second predetermined time period may be the same length as the first predetermined time period. If subsequent wave detector output pulses occur within the second predetermined time period, the delay circuit output 80 remains in its "0" state. If, however, the time period between successive wave detector output signal pulses increases, i.e., if no wave detector output signal pulses occur within the second predetermined time period, then the delay circuit 56 output 80 switches from its "0" state to its high, or "1" state.

It is thus seen that so long as high slew rate output pulses of predetermined number and frequency are received by the delay circuit 56, then the zero-crossing detector 6 is uncoupled from, and the slew rate detector 4 is coupled to, the digital rate comparator output circuit 12. If, however, the number of high slew rate output signals falls below a predetermined level, in a predetermined time period, then the coupling circuit 10 couples the zero-crossing detector 6 with the digital rate comparator output circuit 12. Such zero-crossing detector 6 remains coupled to the output circuit 12 until the double-duty delay circuit 56 again switches state, as described above.

The coupling circuit 10 of the present invention thus ensures that when the ECG signal is characterized by "spiky," or high slew rate waveforms, the slew rate detector 4 is used to monitor the ECG signals. On the other hand, if the slew rate of the incoming ECG signal is more sinusoidal, then the coupling circuit 10 couples the zero-crossing detector 6 to the output circuit 12. This alternate switching between the detectors 4 and 6 ensures a reliable and accurate count of the heart beats.

It should be apparent that some heart beats might be missed. For example, the initial wave detector output signals from the multivibrator 36, which are provided to the double-duty delay circuit 56, will not be enabled by the AND gate 42 to pass to the OR gate 54, since the AND gate 42 is not enabled until after a first predetermined time period. Generally, the first predetermined time period is set between 1 and 5 seconds, with the 2-5 seconds preferred. (Although such high slew rate signals may not be counted by the slew rate detector circuit 4, it is still possible that they may be counted by the zero-crossing detector 6, if they happen to be passed by the low-pass filter 47.) Similarly, if the AND gate 42 is enabled after a first predetermined time period, and then no further high slew rate signals are received, the zero-crossing detector will be disenabled for at least a second predetermined period of time and any heart beats of low slew rate will be missed. As a practical matter, however, the number of heart beats that are missed by the heart rate detector circuit 2 will be relatively small since the double-duty delay circuit 56 is designed so that the first and second predetermined time periods are not so great that the missed heart beats would have a critical effect. Moreover, also as a practical matter, it is unlikely that a patient's ECG waveform will be drastically alternating between high and low slew rates in such a manner that a critical number of heart beats will be missed.

The output circuit 12 includes a digital rate comparator 86. The digital rate comparator is of conventional design (such as including a digital magnitude comparator, a latch and a counter) and has an input 88 coupled with the output line 69 of the OR gate 54 from the coupling circuit 10. The signals at the input 88 reflect the number of heart beats from either the zero-crossing detector 6 or the slew rate detector 4. The digital rate comparator 86 includes program rate input terminals 90 for reading into the digital rate comparator a predetermined, or preprogrammed, rate. The digital rate comparator 86 receives the heart beat signals and determines, on a beat-by-beat basis, the actual heart rate. This heart rate is compared with the programmed rate and when the heart rate exceeds the programmed rate, a comparator output signal is provided on the comparator output line 92. Delay circuit 93, which could be an integrator as is well known in the art, integrates the comparator output signals over a predetermined time and provides a detector output signal on line 14 if the number of comparator output rate signals exceeds a predetermined number in a predetermined time. Generally, the delay circuit 93 provides a safety feature to prevent spurious signals from starting the defibrillating pulse generator. The delay circuit 93 may provide an output signal if two comparator output pulses are received within a four second interval.

The digital rate comparator 86 also includes readout terminals 94 for reading out the actual heart rate. This actual heart rate readout may not be needed for defibrillator or pacer operations, but circumstances may exist where the actual rate is desired. If the device is implanted in a human body, the readout can be by telemetry or the like.

When the heart rate detector 2 is used in a defibrillator circuit, as shown in FIG. 1, the detector output signal on line 14 is provided to the inputs of two AND gates 96 and 98. AND gate 96 has, as its other input, the output from the PDF circuit 16. The output of AND gate 96 is coupled to an OR gate 100 which, in turn, is coupled to a defibrillator pulse generator (not shown) to initiate a defibrillating shock. Thus, when the PDF circuit characteristics are satisfied and the heart rate output exceeds a predetermined value, the AND gate 96 is enabled, and the PDF circuit is coupled with the defibrillating pulse generator.

Under certain circumstances, a defibrillating shock may be desired solely dependent upon abnormal heart rate. Under such conditions, AND gate 98 has, at terminal 102, a high or "1" input to enable the defibrillating pulse generator to be activated solely by the output 14 of the heart rate detector circuit. If such feature is not desired, then the terminal 102 of the AND gate 98 has an inhibit or "0" input.

While preferred forms and arrangements of the invention have been shown and illustrated, it is to be clearly understood that various changes in detail and arrangement may be made without departing from the spirit and scope of this disclosure.

What is claimed is:

1. A heart beat rate detector responsive to incoming ECG signals comprising:
   input means for receiving an ECG signal;
   wave detector means operatively coupled with the input means for detecting an ECG waveshape having a slew rate above a predetermined threshold and providing a wave detector output signal for each detected waveshape;
   zero-crossing detector means operatively coupled with the input means for detecting an ECG waveshape having a predetermined amplitude and providing a zero-crossing output signal for each detected waveshape;
   output means for receiving the wave detector output signal and zero-crossing output signal; and
   coupling means for selectively coupling only one of said wave detector means and zero-crossing means with said output means.

2. The detector of claim 1, wherein said wave detector means provides no more than one wave detector output signal per cardiac cycle.

3. The detector of claim 2, wherein said coupling means selectively couples only one of said wave detector means and zero-crossing means with said output means dependent upon the rate of wave detector output signals provided by the wave detector means.

4. The detector of claim 3, wherein said coupling means couples said wave detector means with said output means when the rate of wave detector output signals exceeds a predetermined value.

5. The detector of claim 3, wherein said coupling means couples said wave detector means with said output means when the number of wave detector output signals exceeds a predetermined value for a first predetermined time period, and the spacing between such wave detector output signals is substantially constant.

6. The detector of claim 5, wherein said coupling means retains said wave detector means coupled with said output means for at least a second predetermined time period.

7. The detector of claim 5, wherein said coupling means retains the wave detector means coupled with said output means until no wave detector output signals are received in at least a second predetermined time period.

8. The detector of one of claim 4, 5, 6, or 7, wherein said coupling means couples said zero-crossing means with said output means when said wave detector means is not coupled with said output means.

9. The detector of claim 1, wherein said wave detector means comprises means for differentiating the ECG signal and for taking the absolute value of the differentiated signal to obtain the slew rate, comparing means for comparing the slew rate with a predetermined slew rate threshold to provide a slew rate output signal when the detected slew rate exceeds the slew rate threshold.

10. The detector of claim 9, wherein said wave detector means further comprises means responsive to the slew rate output signal for generating the wave detector output signal.

11. The detector of claim 10, wherein said means for generating the wave detector output signal comprises a monostable multivibrator means for providing a single, uniform wave detector output pulse in response to each slew rate output signal.

12. The detector of claim 11, wherein said monostable multivibrator means is responsive to no more than one slew rate output signal per cardiac cycle.

13. The detector of claim 11, wherein said monostable multivibrator means is responsive to no more than one slew rate output signal in a predetermined refractory time period.

14. The detector of claim 13, wherein said monostable multivibrator means includes means for varying the predetermined refractory time period dependent upon the cardiac cycle to be monitored.

15. The detector of claim 1, wherein said output means comprises a comparator means for determining the aggregate number of wave detector output signals and zero-crossing detector output signals received per unit of time, and comparing the aggregrate number per unit of time with a predetermined rate.

16. The detector of claim 15, wherein said comparator means includes heart rate output means for providing an output signal of the aggregate signals received per unit of time, said output signal being the actual heart rate.

17. The detector of claim 15, wherein said comparator means includes a comparator output means for providing a comparator output signal when the aggregate signals per unit of time exceed a predetermined rate.

18. The detector of claim 15, wherein said comparator means compares the aggregate signals per unit of time with a predetermined rate on a beat-by-beat basis.

19. The detector of claim 15, wherein said comparator means includes a comparator output means for providing a series of comparator output signals when the aggregate signals per unit of time exceed the predetermined rate on a beat-by-beat basis.

20. The detector of claim 19, wherein said comparator means further comprises integrating means for integrating the series of comparator output signals over a predetermined time period and providing a detector output signal when the integrated series of comparator output signals exceed a predetermined value.

21. A heart beat rate detector responsive to incoming ECG signals over a number of cardiac cycles, each cardiac cycle including a wave packet of P, Q, R, S and T waves, each wave packet representing a heart beat, wherein said detector comprises:

first detecting means for detecting a wave packet by detecting a first characteristic of said wave packet and providing a first output signal when said wave packet is detected;

second detecting means for detecting a wave packet by detecting a second characteristic of said wave packet and providing a second output signal when said wave packet is detected;

output means for receiving the first and second output signals; and coupling means for selectively coupling only one of said first and second detecting means with said output means whereby the aggregate number of first and second output signals represents the number of heart beats.

22. The detector of claim 21, wherein the first detecting means detects a wave packet having a rate of change of voltage versus time greater than a predetermined threshold value.

23. The detector of claim 21 or 22, wherein the second detecting means detects a wave packet having an R-wave amplitude greater than a predetermined amplitude.

24. The detector of claim 21, wherein said first detecting means includes means for detecting the rate of change of the P, Q, R, S and T waves in each wave packet, comparing the rate of change with a predetermined threshold value, and providing a single first output signal for each wave packet when the rate of change of any of the P, Q, R, S and T waves in the wave packet exceeds the predetermined threshold value.

25. The detector of claim 21 or 24, wherein said second detecting means includes a comparator means for comparing the amplitude of the R-wave within a wave packet with a predetermined amplitude and providing a second output signal when the R-wave amplitude exceeds the predetermined amplitude.

26. The detector of claim 25, wherein said second detecting means comprises a high gain amplifier.

27. The detector of claim 24, wherein said coupling means couples only said first detecting means with said output means when a predetermined number of first output signals occur at a substantially constant frequency over a first predetermined time period and retains said first detecting means coupled with the output means for at least a second predetermined time period.

28. The detector of claim 27, wherein said coupling means couples said second detecting means with said output means whenever the first coupling means is not coupled with said output means.

29. A system for use with an automatic defibrillator for defibrillating the heart of a patient experiencing abnormal cardiac rhythm, comprising:

input means for receiving ECG waveforms;

processing means coupled with said input means for processing the ECG waveforms in accordance with a probability density function to develop a probability density function output signal;

a heart rate detector coupled between said input means and a processing output means, said heart rate detector comprising, first detecting means for detecting an ECG wave packet by detecting a first characteristic of said wave packet and providing a first output signal when said wave packet is detected;

second detecting means for detecting an ECG wave packet by detecting a second characteristic of said wave packet and providing a second output signal when said wave packet is detected;

rate detector output means for receiving the first and second output signals and for providing a rate detector output signal to the processing output means when the aggregate number of first and second output signals exceed a predetermined rate; and coupling means for selectively coupling only one of said first and second detecting means with said rate detector output means whereby the aggregate number of first and second output signals represents the number of heart beats; and processing output means for coupling said processing means and heart rate detector with a defibrillating pulse generator for initiating the discharge of a defibrillating shock upon receiving a predetermined signal from at least one of said processing means and said heart rate detector.

30. The system of claim 29, further comprising means for coupling said rate detector output means to said processing output means wherein the rate detector output signal initiates the defibrillating pulse generator to deliver a shocking pulse to the patient's heart.

31. The system of claim 29, wherein the first detecting means detects a wave packet having a rate of change of voltage versus time greater than a predetermined threshold value.

32. The system of claim 29 or 31, wherein the second detecting means detect a wave packet having an R-wave amplitude greater than a predetermined amplitude.

33. The system of claim 29, wherein said first detecting means includes means for detecting the rate of change of the P, Q, R, S and T waves in each wave packet, comparing the rate of change with a predetermined threshold value, and providing a single first output signal for each wave packet when the rate of change of any of the P, Q, R, S and T waves in the wave packet exceeds the predetermined threshold value.

34. The system of claim 29 or 33, wherein said second detecting means includes a comparator means for comparing the amplitude of the R-wave within a wave packet with a predetermined amplitude and providing a second output signal when the R-wave amplitude exceeds the predetermined amplitude.

35. The system of claim 34, wherein said second detecting means comprises a high gain amplifier.

36. The detector of claim 33, wherein said coupling means couples only said first detecting means with said rate detector output means when a predetermined number of first output signals occur at a substantially constant frequency over a first predetermined time period and retains said first detecting means coupled with the rate detector output means for at least a second predetermined time period.

37. The system of claim 36, wherein said coupling means couples said second detecting means with said rate detector output means whenever the first coupling means is not coupled with said rate detector output means.

* * * * *